United States Patent
Baltimore

(10) Patent No.: US 7,479,291 B1
(45) Date of Patent: Jan. 20, 2009

(54) HAIR PRODUCT

(76) Inventor: Janice D Baltimore, 5006 Leroy Gorham Dr., Capitol Heights, MD (US) 20743

( * ) Notice: Subject to any disclaimer, the term of this patent is extended or adjusted under 35 U.S.C. 154(b) by 0 days.

(21) Appl. No.: 11/936,476

(22) Filed: Nov. 7, 2007

(51) Int. Cl.
*A01N 65/00* (2006.01)
(52) U.S. Cl. ................................ 424/725
(58) Field of Classification Search ........... None
See application file for complete search history.

(56) References Cited

U.S. PATENT DOCUMENTS

2001/0012895 A1* 8/2001 McIver et al. .............. 546/22
2005/0053564 A1* 3/2005 Lieberman ............... 424/70.13
2007/0275022 A1* 11/2007 Satou et al. ............... 424/401

FOREIGN PATENT DOCUMENTS

GB 2289219 A * 11/1995
JP 09040531 A * 2/1997

* cited by examiner

*Primary Examiner*—Michael V Meller
*Assistant Examiner*—Qiuwen Mi
(74) *Attorney, Agent, or Firm*—Michael L. Greenberg, Esq.; Greenberg & Lieberman, LLC

(57) ABSTRACT

A fragrant chemical composition for fashioning hair consisting of shea butter, glyceride, triclosan and menthol that combines to aid in the pressing of hair in a well conditioned and healthful manner, as well as to prevent itching typically associated with certain hair fashions such as braids and dreadlocks. The chemical composition protects these hair fashions, as well as hair color, through varying percentages of natural elements and elements known to be healthful.

15 Claims, No Drawings

HAIR PRODUCT

FIELD OF THE INVENTION

The present invention is a fragrant product for fashioning hair consisting of shea butter, glyceride, triclosan and menthol that combines to aid in the pressing of hair, as well as to prevent itching typically associated with certain hair fashions such as braids.

BACKGROUND OF THE INVENTION

Hair fashion has always been a fundamental part of society. Adults and children alike keep up with hair trends and even strive to set these trends. Hair fashion accessories also have become a lucrative business as companies compete for shares of the hair fashion market. Hair braiding is one area of hair fashion that has maintained cultural and social longevity.

Hair braiding is common for people of all walks of life. The process is most prevalent with people of African heritage, although people of other races and ethnicities also engage in hair braiding. The hair braiding process is often arduous and times consuming as designated groupings of hair are tightly pressed together to create a single braid. But the hair braiding process does not end once all the desired hair groupings are completed. People must take care in order to keep the braids intact. They also must resist the urge to play with the braids, despite the fact that hair braids are often so tight at the scalp that it can become itchy and somewhat uncomfortable at times.

Other issues relating to hair braiding concern color retention for dyed hair and breakage of individual braids. Washing braided hair places individual braids in jeopardy, as does dryness, which can be unhealthy and damaging for braided hair. Moreover, mineral oil's benefits to existing products is often outweighed by the fact that it is known to diminish or even remove color from dyed hair. Various products attempt to alleviate some of these issues, but there remains a need for a chemical composition that can keep the scalp moisturized while protecting the physical makeup of the braids while not causing additional itching.

One product that attempts to treat the hair and scalp is known as Sulfur 8™. This product is commonly used on hair, including braided hair, for its purported effects on stopping itching, hair restoration and dandruff removal. This and similar products include such active chemicals as petroleum, lanolin, mineral oil, menthol, triclosan and fragrance. However, products such as Sulfur 8™ are commonly criticized for possessing a foul and relatively unpleasant odor. Due to this fact, there is a need for a product that enhances the positive effects of such existing items but trades the unpleasant odor for a more pleasant fragrance. In addition to the unpleasant odor associated with existing products, these existing products also end up forming a waxy coating on the hair and scalp that can cause a matted effect on hair. This results in additional itching if left untreated. A chemical composition is needed in the market to alleviate this unhealthy issue in order to maintain the physical qualities of the person's hair.

The present invention satisfies the aforementioned needs through its unique chemical composition. Elements of existing concoctions are enhanced and expanded upon with the additional combination of ingredients employed by the present invention. The incorporation of glyceride serves a moisturizer that aids in the protection, comfort and physical maintenance of a person's hair. Shea butter also solves the typical problem of braid breakage by offering a more substantial protection to that as well as retention of color for dyed hair. Moreover, the addition of shea butter—an organic substance—also masks the traditional unpleasant odor associated with similar hair products. Because of these differences, the present invention is unique and necessary to those desiring to combine healthy hair with fashion style.

SUMMARY OF THE PRESENT INVENTION

The present invention is a fragrant product for fashioning hair consisting at a minimum of shea butter, glyceride, triclosan and menthol. This composition combines to aid in the pressing of hair, as well as to prevent itching typically associated with certain hair fashions. The novel combination of the present invention provides people with a product that protects braided and otherwise styled hair in a manner that is free any sort of pungent odor.

DETAILED DESCRIPTION OF THE PRESENT INVENTION

The present invention is a mixture of various compounds that come together to form a product for pressing and maintaining certain hairstyles such as braids or dreadlocks. The preferred embodiment of the present invention consists of menthol, shea butter, glyceride and triclosan. These chemical compositions are merged together to ultimately create a soft product for use on a person's hair and scalp. The effects of this mixture when applied to a person's hair or scalp is that the hairstyle such as braids or dreadlocks will remain strong and intact without the burdens of itching or foul odor. In addition, the chemical mixture of the present invention also serves to maintain the physical and color integrity of the man or woman's hair.

Each chemical composition of the present invention brings a positive quality to the ultimate goals of the product. The chemical compositions are such that the overall present invention maintains an optimal physical consistency for the person. This consistency is absorbed into the hair and scalp without creating mats or oily clumps, and is particularly effective for braided hair or dreadlocks. The consistency is based on the percentage ranges of the chemical compositions of the present invention.

Menthol consists of about 35 percent of the overall chemical composition of the present invention. Menthol is a covalent organic compound used for its anesthetic qualities. Menthol also is used in the present invention for its natural ability to counter traditional irritating factors associated with styling hair. In this manner, the menthol plays a role in the overall present invention in that the person will not have to endure itching and minor scalp trauma that is typically related to the tightness of the braids or dreadlocks.

Shea butter consists of about 25 percent of the overall chemical composition of the present invention. Shea butter is a natural oil derived from seeds of shea trees. Shea butter is included in the present invention for its natural ability to vitalize the scalp and hair. Shea butter is a source for Vitamin A, which works under the auspices of the present invention to protect and maintain healthful attributes to the hair and scalp. In this regard, the shea butter element of the present invention prevents breakage of the hair or braids when these hairstyles are fashioned. In addition, shea butter's qualities assist in retaining other physical hair characteristics such as color if the hair is dyed. Vitamin E also is sourced from shea butter, which adds additional healthful benefits to the fashioned hair and scalp. Substantial moisturizing qualities of shea butter also maintain the natural attributes of fashioned hair.

Shea butter also has a distinct smell. The smell of shea butter can be altered through various refining processes such as clay. However, the preferred embodiment of the present invention seeks to utilize the natural odor of shea butter. The fragrant natural odor of the shea butter serves to mask and overcome the smells that otherwise might permeate from other chemical compositions of the present invention, particularly menthol.

Glyceride chemical compositions also serve to attract moisture toward the scalp and hair for even more protection. This protection associated with the glyceride chemical composition of the present invention works as an additional chemical agent for maintaining the physical qualities of the braided hair and scalp. Glyceride chemical composition also helps softens the person's hair by its ability to absorb moisture from the air. Glyceride chemical composition makes up about 20 percent of the present invention's overall composition.

Triclosan comprises about 20 percent of the overall composition of the present invention. Triclosan is used in the present invention primarily as an anti-bacterial agent. In this manner, triclosan assists the overall chemical composition of the present invention in maintaining healthy hair and scalp.

TABLE 1

| | |
|---|---|
| Menthol | 35% |
| Shea Butter | 25% |
| Glyceride | 20% |
| Triclosan | 20% |

In Table 1, we see the amounts of each chemical compound mixed together for the present invention. These amounts and percentages can vary by a few percentage points in order to cater to people featuring different types, quality levels and standards relating to hair and skin.

In Table 2, we see an additional embodiment of the present invention. In this embodiment, there is about a percent less of triclosan as there is in the preferred embodiment. However, 0.5 percent of lanolin and 0.5 percent of petroleum are included in this additional embodiment.

Lanolin is included for its ability to serve as an ointment to assist in the enhanced quality of the braided hair and scalp. Moreover, lanolin is used in conjunction with the overall present invention in this additional embodiment for its natural ability to aid in the hair pressing process. Petroleum also may be used for the hair pressing process.

TABLE 2

| | |
|---|---|
| Menthol | 35% |
| Shea Butter | 25% |
| Glyceride | 20% |
| Triclosan | 19% |
| Petroleum | .5% |
| Lanolin | .5% |

An additional embodiment of the present invention includes incorporating a known and conventional color additive into the overall embodiments of the present invention as stated above. Since the ideal color for the overall present invention is green, one example of a known color additive to be used is D&C Green No. 5. The overall percentage of the color additive would be no more than 3 percent of the overall present invention.

Another additional embodiment of the present invention relates to the use of B5 or panthenol. B5 or panthenol serves as a conditioning and color-saving element that can be added to the overall present invention. Panthenol is a derivative of B5 and is the suggested element for this additional embodiment of the present invention. This extra conditioning element is meant to provide the person with an additional avenue for color maintenance and is meant to be an option for those with dyed or colored hair. The overall percentage of the color-saving element would be no more than 3 percent of the overall present invention.

I claim:

1. A hair and scalp grooming composition, consisting of:
   menthol;
   shea butter;
   glyceride; and
   triclosan.

2. The composition of claim 1, wherein said menthol is greater than 30 percent and less than 40 percent of the overall composition.

3. The composition of claim 1, wherein said shea butter is greater than 20 percent and less than 30 percent of the overall composition.

4. The composition of claim 1, wherein said glyceride is greater than 15 percent and less than 25 percent of the overall composition.

5. The composition of claim 1, wherein said triclosan is greater than 15 percent and less than 25 percent of the overall composition.

6. The composition of claim 1, wherein said menthol is greater than 30 percent and less than 40 percent of the overall composition; wherein said shea butter is greater than 20 percent and less than 30 percent of the overall composition;
   wherein said glyceride is greater than 15 percent and less than 25 percent of the overall composition; and
   wherein said triclosan is greater than 15 percent and less than 25 percent of the overall composition.

7. A hair and scalp grooming composition, consisting of: menthol; shea butter; glyceride; triclosan; petroleum; and lanolin.

8. The composition of claim 7, wherein said menthol is greater than 30 percent and less than 40 percent of the overall composition.

9. The composition of claim 7, wherein said shea butter is greater than 20 percent and less than 30 percent of the overall composition.

10. The composition of claim 7, wherein said glyceride is greater than 15 percent and less than 25 percent of the overall composition.

11. The composition of claim 7, wherein said triclosan is greater than 14 percent and less than 24 percent of the overall composition.

12. The composition of claim 7, wherein said petroleum is greater than 0.3 percent and less than 0.7 percent of the overall composition.

13. The composition of claim 7, wherein said lanolin is greater than 0.3 percent and less than 0.7 percent of the overall composition.

14. A hair and scalp grooming composition, consisting of: menthol; shea butter; glyceride; triclosan; petroleum; lanolin; and panthenol;
   wherein said menthol is greater than 30 percent and less than 40 percent of the overall composition;
   wherein said shea butter is greater than 20 percent and less than 30 percent of the overall composition;
   wherein said glyceride is greater than 15 percent and less than 25 percent of the overall composition;

wherein said triclosan is greater than 15 percent and less than 25 percent of the overall composition;

wherein said petroleum is greater than 0.3 percent and less than 0.7 percent of the overall composition;

wherein said lanolin is greater than 0.3 percent and less than 0.7 percent of the overall composition; and wherein said panthenol is greater than 0.3 percent and less than 3 percent of the overall composition.

15. The composition of claim 14, further consisting of a color additive that is greater than 0.1 percent and less than 3 percent of the composition.

* * * * *